(12) United States Patent
Ikeda et al.

(10) Patent No.: US 6,258,554 B1
(45) Date of Patent: Jul. 10, 2001

(54) METHOD FOR PRODUCING METABOLITES BIOLOGICALLY SYNTHESIZED VIA PHOSPHORIBOSYL PYROPHOSPHATE

(75) Inventors: Masato Ikeda, Yamaguchi (JP); Kazuyuki Okamoto, Veracrus (MX); Tetsuo Nakano; Nozomu Kamada, both of Yamaguchi (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/347,808

(22) Filed: Jul. 22, 1999

(30) Foreign Application Priority Data

Jul. 3, 1998 (JP) .................................. 10-187992

(51) Int. Cl.⁷ .............................. C12P 1/00; C12P 25/00; C12Q 1/48; C12N 9/10; C12N 1/20
(52) U.S. Cl. ................. 435/41; 435/15; 435/66; 435/193; 435/252.3; 435/320.1; 435/840; 435/843; 435/848; 536/23.2
(58) Field of Search ................. 435/41, 66, 15, 435/193, 252.3, 320.1, 840, 843, 848; 536/23.2

(56) References Cited

U.S. PATENT DOCUMENTS 5,168,056   12/1992   Frost .................................. 435/172.3
5,589,355   12/1996   Koizumi et al. ....................... 435/66

FOREIGN PATENT DOCUMENTS 19644567   4/1998   (DE) .
600 463    6/1994   (EP) .
98/18937   5/1998   (WO) .

OTHER PUBLICATIONS

Biotechnology & Genetic Engineering Reviews, vol. 2, pp. 175–213 (1984).
J. Bacteriol, vol. 175, No. 17, p. 5375–5383 (1993).
Biochimica et Biophysica Acta, vol. 1216, pp. 307–310 (1993).
Biochemistry, vol. 12, No. 10, pp. 1969–1971 (1973).
J. Bacteriol, vol. 98, No. 3, pp. 1151–1158 (1969).
Chemical Abstracts, vol. 67, No. 9, Aug. 28, 1967, No. 41631, XP–002119105.

*Primary Examiner*—Tekchand Saidha
(74) *Attorney, Agent, or Firm*—Fitzpatrick, Cella, Harper & Scinto

(57) ABSTRACT

An industrially more advantageous method for the production of metabolites biologically synthesized via phosphoribosyl pyrophosphate (PRPP) is provided, making use of metabolically modified strains in which transketolase activity is deficient or reduced in comparison with the parent strain.

8 Claims, 1 Drawing Sheet

US 6,258,554 B1

Figure 1:
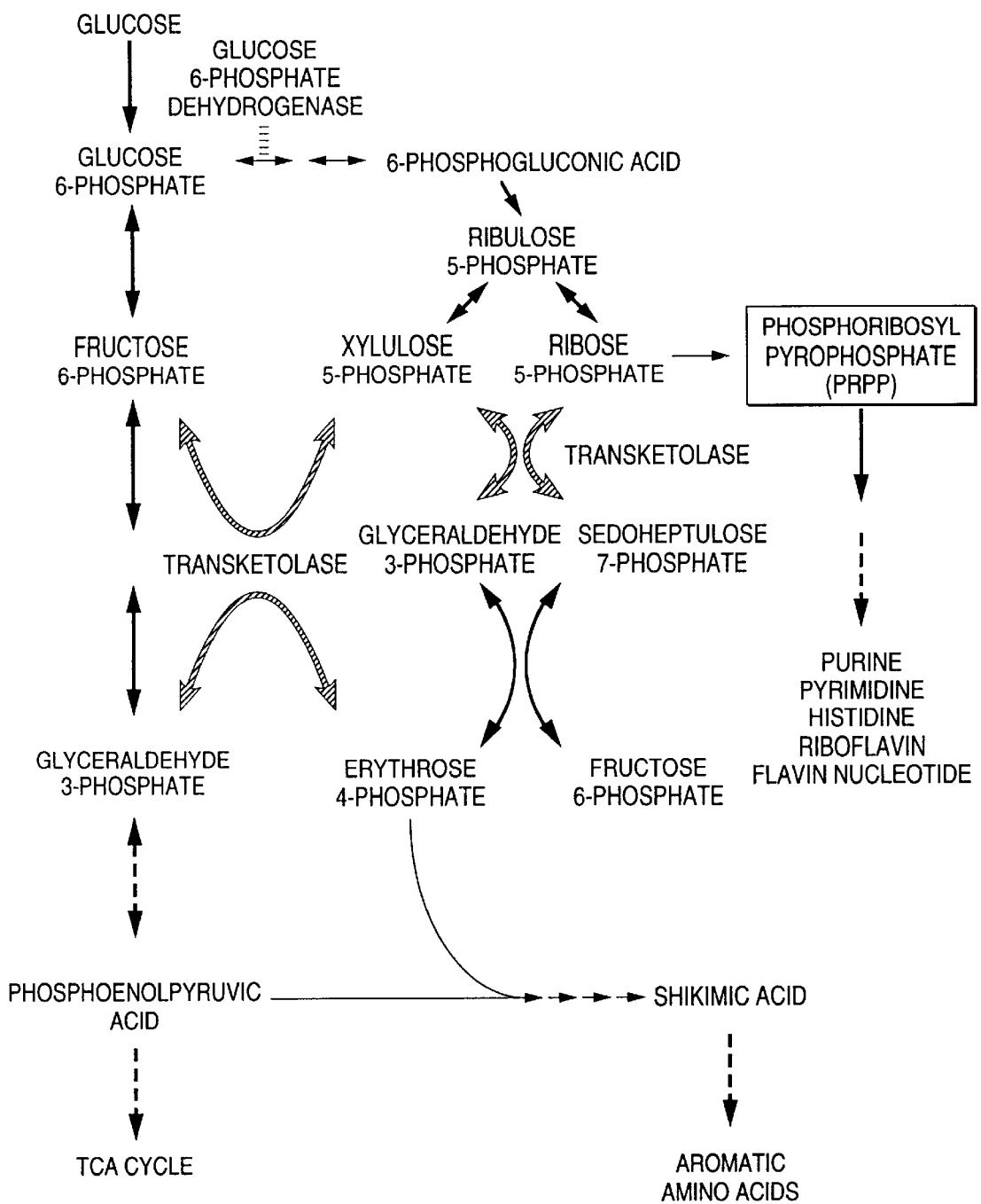

METHOD FOR PRODUCING METABOLITES BIOLOGICALLY SYNTHESIZED VIA PHOSPHORIBOSYL PYROPHOSPHATE

FIELD OF THE INVENTION

This invention relates to a method for the production of useful substances which are synthesized by a fermentation method on the biosynthetic pathway from phosphoribosyl pyrophosphate (referred to as "PRPP" hereinafter) using a metabolically modified strain which is entirely transketolase activity-deficient or which has reduced transketolase activity compared to the parent strain.

BACKGROUND OF THE INVENTION

Examples of useful substances synthesized from PRPP on the microbial metabolic pathway include nucleic acid-related substances such as purine nucleotides, pyrimidine nucleotides, purine nucleosides, pyrimidine nucleosides, purine bases, pyrimidine bases and flavin nucleotides, as well as L-histidine and riboflavin.

These nucleic acid related substances, L-histidine, riboflavin and the like have been produced industrially by a fermentation method or by a combination of a fermentation method with a synthetic method. See Applied Microbiology, edited by Shoichi Takao et al., Buneido Shuppan (1996); Amino Acid Fermentation, edited by Hiroshi Aida et al., Gakkai Shuppan Center (1986); JP-A-6-225776 ("JP-A" as used herein means an "Japanese Published Unexamined Patent Application").

In microorganisms, PRPP is biologically synthesized by a PRPP synthetase from ribose 5-phosphate which is an intermediate in the pentose phosphate pathway.

As the biosynthetic pathways of ribose 5-phosphate, an oxidative pentose phosphate pathway via glucose 6-phosphate dehydrogenase is known, and it is expected that a non-oxidative pentose phosphate pathway is also involved in its biosynthesis because all of the enzymes on the non-oxidative pentose phosphate pathway via transketolase reaction are reversible (see FIG. 1).

It has been determined by a study of the metabolism of labeled glucose that both of these pathways are concerned in the biosynthesis of ribose 5-phosphate in *Escherichia coli*, see *Biochemistry*, 12, 10, 1969 (1973). Also, it has been shown by genetic studies that ribose 5-phosphate is provided by the non-oxidative pentose phosphate pathway via transketolase reaction, because glucose 6-phosphate dehydrogenase-deficient strains of *Escherichia coli* and *Corynebacterium glutamicum* do not show ribose auxotrophy, see D. G. Fraenkel and R. T. Vinopal, *Ann. Rev. Microbiol.*, 27, 69–100 (1973); E. D. Ihnen and A. L. Demain, *J. Bacteriol.*, 98, 1151–1158 (1969).

This information suggests that increase in the activity of transketolase enables increased supply of ribose 5-phosphate and PRPP from the non-oxidative pathway and therefore the amount of substances biologically synthesized from PRPP is increased.

In addition, it has been reported that a transketolase activity-deficient strain in inosine-producing strains belonging to the genus Bacillus such as *Bacillus subtilis* accumulates a considerable amount of ribose in the culture medium so that the yield of purine nucleotide production is reduced, see K. Sasajima and M. Yoneda, *Biotechnol. Genet. Eng. Rev.*, 2, 175–213 (1984).

This information also suggests that the activity of transketolase is necessary for the production of substances biologically synthesized from PRPP. However, to date, with respect to all microorganisms, it has not been known that the production yield of metabilites to be biologically synthesized via PRPP is improved by having transketolase activity lost or reduced.

Since demands have been increasing for metabolites biologically synthesized via PRPP, particularly nucleic acid-related substances, L-histidine and riboflavin and the like, the development of an industrially advantageous method for their production is strongly desired.

SUMMARY OF THE INVENTION

The object of the present invention is to provide an industrially more advantageous method for the production of metabolites biologically synthesized via PRPP.

In conventional studies on the breeding of microorganisms, great achievement has been made by the enhancement of metabolism of the terminal biosynthetic pathway concerned in the biosynthesis of each metabolite of interest.

The inventors of the present invention have considered that other modification than metabolic enhancement of terminal biosynthetic pathway, namely modification of the central metabolism capable of increasing supply and pooling of the starting substrate, would be necessary for further improvement of the productivity of metabolites, and conducted extensive studies on the influence of carbon flow upon various metabolites by manipulating the central metabolic pathway in microorganisms.

As a result, it was found that the production efficiency of metabolites biologically synthesized via PRPP in the biosynthetic pathway can be improved by making transketolase activity to be deficient or reduced in comparison with that of a parent strain thereof, thus resulting in the accomplishment of the present invention.

Accordingly, it is an object of the present invention to provide:

(1) a method for increasing productivity of metabolites biologically synthesized via phosphoribosyl pyrophosphate on the metabolic pathway in a microorganism, which comprises making transketolase activity in a microorganism belonging to the genus Corynebacterium, Brevibacterium or Escherichia to be deficient or reduced in comparison with that of a parent strain thereof;

(2) a method for producing metabolites, which comprises culturing in a medium a microorganism belonging to the genus Corynebacterium, Brevibacterium or Escherichia in which transketolase activity is deficient or reduced in comparison with a parent strain thereof until one or a plurality of metabolites selected from metabolites biologically synthesized via phosphoribosyl pyrophosphate on the metabolic pathway is formed and accumulated in the culture, and recovering said metabolites therefrom;

(3) the method according to (1) or (2) above, wherein the metabolite is selected from the group consisting of purine nucleotides, pyrimidine nucleotides, purine nucleosides, pyrimidine nucleosides, purine bases, pyrimidine bases, flavin nucleotides, L-histidine and riboflavin;

(4) the method according to (1) or (2) above, wherein said microorganism is selected from the group consisting of *Corynebacterium glutamicum* TKT6, *Corynebacterium glutamicum* TKT6/pPH8, *Corynebacterium glutamicum* TKT6/pFM41 and *Escherichia coil* AI80/pFM201;

(5) a microorganism belonging to the genus Corynebacterium or Brevibacterium, in which transketolase activity is deficient or reduced in comparison with a parent strain thereof; and (6) the microorganism according to (5) above, wherein said microorganism is selected from the group consisting of *Corynebacterium glutamicum* TKT6, *Corynebacterium glutamicum* TKT6/pPH8 and *Corynebacterium glutamicum* TKT6/pFM41.

BRIEF DESCRIPTION OF THE INVENTION

FIG. 1 is a graph showing the metabolic pathway from glucose to PRPP. In FIG. 1, gray arrows show reactions by transketolase.

DETAILED DESCRIPTION OF THE INVENTION

The following describes the present invention in detail.

The phrase "microorganism in which transketolase activity is reduced in comparison with a parent strain thereof" as used herein includes all the strains showing any degree of reduced transketolase activity in comparison with a parent strain as measured under the conditions described in the Examples below. Reduction in the transketolase activity is preferably 30% or more, more preferably 50% or more. Examples of the strains in which transketolase activity is deficient or reduced include the strains having one or more nucleotide modification(s) causing deficiency or reduction in the transketolase activity, which modifications are selected from nucleotide substitutions, deletions, insertions, additions, and inversions in the nucleotide sequence of the transketolase structural gene or the gene that participates in transcription or translation of the transketolase structural gene.

The microorganism to be used in the present invention is any one of wild strains, mutant strains, cell fusion strains, transduced strains or recombinant strains constructed by means of recombinant DNA techniques, so long as it belongs to the genus Corynebacterium, Brevibacterium or Escherichia, and so long as transketolase activity of the microorganism is deficient or reduced in comparison with a parent strain thereof.

Examples of the microorganisms include *Corynebacterium glutamicum*, *Corynebacterium acetoacidophilum*, *Corynebacterium herculis*, *Corynebacterium lilium*, *Corynebacterium melassecola*, *Brevibacterium divaricatum*, *Brevibacterium flavum*, *Brevibacterium immmariophilum*, *Brevibacterium lactofermentum*, *Brevibacterium thiogenitalis* and *Escherichia coli*, in which transketolase activity is deficient or reduced in comparison with a parent strain thereof.

Preferred examples of the microorganisms to be used as the parent in the present invention include so-called coryne-type glutamic acid producing strains and *Escherichia coli* which are used in the amino acid fermentation and *Corynebacterium ammoniagenes* which is used in the nucleic acid fermentation and riboflavin fermentation.

The microorganism of the present invention can be obtained from a known microorganism which belongs to the genus Corynebacterium, Brevibacterium or Escherichia, by inducing mutation which causes deficiency or reduction of the transketolase activity in known microorganisms by a usual mutation treatment method, a gene replacement method by recombinant DNA techniques, a transduction method or a cell fusion method.

As illustrative examples, the strain of the present invention can be obtained by selection using shikimic acid auxotrophy and ribose non-assimilating property as the markers.

After subjecting a microorganism belonging to the genus Corynebacterium, Brevibacterium or Escherichia to the usual mutation treatment, such as ultraviolet ray irradiation or chemical treatment with N-methyl-N'-nitro-N-nitrosoguanidine (NTG) or nitrous acid, shikimic acid-auxotrophic mutants are obtained by isolating colonies which cannot grow or show poor growth on a minimal medium containing glucose as the sole carbon source, on which the parent strain can grow, but show good growth on said minimal medium supplemented with shikimic acid.

Each shikimic acid-auxotrophic mutant is spread on a minimal medium containing shikimic acid and glucose or ribose as the sole carbon source, and the mutant strain which can grow on the glucose medium but cannot grow or shows poor growth on the ribose medium is selected. Such a strain is a mutant in which transketolase activity is deficient or reduced in comparison with a parent strain thereof.

By this method, a mutant having shikimic acid auxotrophy and ribose non-assimilating property, in which transketolase activity is deficient or reduced in comparison with a parent strain thereof, can be obtained readily. Also, a transketolase activity deficient or reduced mutant strain can be obtained by the usual gene replacement method using a transketolase gene in which a gene encoding transketolase is destroyed in vitro.

As the gene coding for transketolase, known genes can be used, see G. A. Sprenger, *Biochim. Biophys. Acta.*, 1216, 307 (1993); A. Iida et al., *J. Bacteriol.*, 175, 5375–5383 (1993); JP-A-6-169785. The DNA sequence of transketolase gene from *Corynebacterium glutamicum* has been submitted to DDBJ/GenBank/EMBL by the inventors of the present invention and has been assigned the accession number AB023377.

Although the strain of the present invention can be obtained by selection using shikimic acid auxotrophy and ribose non-assimilating property as the markers, certain strains having slightly reduced transketolase activity compared with the parent strain do not always have the shikimic acid auxotrophy and ribose non-assimilating property. Such strains, however, are also intended to be exemplified as suitable microorganisms for use in the present invention. That is, the microorganism of the present invention is a microorganism having increased productivity of metabolites biologically synthesized via PRPP on the metabolic pathway.

Such microorganisms can be obtained from a transketolase mutant strain showing shikimic acid auxotrophy, by inducing a reverse mutation in which the shikimic acid auxotrophy is completely disappeared, a reverse mutation in which the shikimic acid auxotrophy becomes leaky or a reverse mutation in which the ribose assimilating property is restored partially or completely.

Illustrative examples of such microorganism include *Corynebacterium glutamicum* TKT6.

In addition, a strain capable of producing the metabolite of interest more efficiently can be obtained from the thus obtained microorganism in which transketolase activity is deficient or reduced in comparison with that of a parent strain thereof, by further using a known method for improving productivity of a metabolite of interest selected from metabolites biologically synthesized via PRPP, such as the method in which a degrading pathway or a branching pathway is blocked or the method in which feed back control of a key enzyme on the biosynthetic pathway is released or the activity of the enzyme is enhanced, making use of mutation or recombinant DNA techniques.

Using the recombinant DNA techniques, a strain having improved productivity of a metabolite of interest can be obtained by transforming a host with a recombinant plasmid containing a gene for the biosynthesis of said metabolite.

Illustratively, a strain capable of producing histidine in a considerable amount can be obtained by introducing a recombinant plasmid containing a histidine biosynthesis gene, such as pPH8, into *Corynebacterium glutamicum* in which transketolase activity is deficient or reduced in comparison with a parent strain thereof. Illustrative examples of such strains include *Corynebacterium glutamicum* TKT6/pPH8.

A strain capable of producing riboflavin in a considerable amount can be obtained by introducing a recombinant plasmid containing a riboflavin biosynthesis gene, such as pFM41, into *Corynebacterium glutamicum* in which is transketolase activity is deficient or reduced in comparison with a parent strain thereof. Illustrative examples of such strains include *Corynebacterium glutamicum* TKT6/pFM41.

A strain capable of producing riboflavin in a considerable amount can also be obtained by introducing a recombinant plasmid containing a riboflavin biosynthesis gene, such as pFM201, into *Escherichia coli* in which transketolase activity is deficient or reduced in comparison with a parent strain thereof. Illustrative examples of such strains include *Escherichia coli* AI80/pFM201.

A strain having improved productivity of a metabolite of interest can also be obtained by using the following mutation methods.

Namely, the method for producing inosine in which adenine auxotrophy and purine analog resistance are endowed [Hakko to Kogyo (Fermentation and Industry), 36, 12, 1036–1048 (1978)], the method for producing inosinic acid in which adenine and guanine auxotrophy and manganese non-sensitive property are endowed [Applied Microbiology, edited by Shoichi Takao et al, Buneido Shuppan (1996)], the method for producing guanosine in which adenine and histidine auxotrophy and the resistance against methionine sulfoxide, psicofuranine and decoynine are endowed [Applied Microbiology, edited by Shoichi Takao et al, Buneido Shuppan (1996)], the method for producing pyrimidine nucleosides such as uridine and cytidine in which resistance against a pyrimidine analog is endowed [*Bioindustry*, 12, 6, 36–43 (1995)], the method for producing bases such as adenine and uracil in which resistance against a purine analog such-as 2-fluoroadenine is endowed [*Nippon Nogei Kagaku Kaishi* (Journal of the Agricultural Chemical Society of Japan), 48, 1, 63–68 (1974) the same journal, 52, 3, 129–133 (1978)], and the method for producing L-histidine in which resistance against a histidine analog such as 2-thiazolealanine or 1,2,4-triazolealanine is endowed [Amino Acid Fermentation, edited by Hiroshi Aida et al., Gakkai Shuppan Center (1986)].

By improving a microorganism in which transketolase activity is deficient or reduced in comparison with a parent strain thereof, making use of these known methods, a strain having improved productivity of a metabolite of interest can be obtained.

One or a plurality of metabolites selected from metabolites biologically synthesized via PRPP on the metabolic pathway can be produced by culturing the microorganism of the present invention in a medium, thereby effecting formation and accumulation of said metabolites in the culture broth, and subsequently recovering said metabolites therefrom.

Culturing of the microorganism of the present invention can be carried out in accordance with a generally used culturing method.

The medium to be used may be either a synthetic medium or a natural medium, with the proviso that it contains appropriate amounts of necessary carbon sources, nitrogen sources, inorganic substances, amino acids and vitamins, as well as trace amounts of nutrient substances required by the strain to be used. When the strain to be used requires shikimic acid for its growth in the medium to be used, a small amount of shikimic acid is added to the medium. The same purpose can also be achieved by adding small amounts of the three aromatic amino acids instead of shikimic acid.

Examples of the carbon source to be used include carbohydrates such as glucose, fructose, sucrose, maltose, mannose, glycerol, starch, starch hydrolysate and molasses, polyalcohols and various organic acids such as pyruvic acid, fumaric acid, lactic acid and acetic acid. Depending on the assimilability of the microorganism, hydrocarbons and alcohols can also be used.

Examples of the nitrogen source include ammonia or various inorganic and organic ammonium salts such as ammonium chloride, ammonium sulfate, ammonium carbonate and ammonium acetate, urea and other nitrogen-containing substances, and nitrogen-containing organic substances such as peptone, NZ-amine, meat extract, yeast extract, corn steep liquor, casein hydrolysate and fish meal or a digest thereof.

Examples of the inorganic substance include potassium dihydrogenphosphate, dipotassium hydrogenphosphate, ammonium sulfate, ammonium chloride, magnesium sulfate, sodium chloride, ferrous sulfate, manganese sulfate and calcium carbonate.

Amino acids and vitamins can be added to the medium as occasion demands depending on the carbon source, nitrogen source and other substances used therein.

The culturing is carried out under aerobic conditions such as shaking culture or aeration agitation culturing. In general, the culturing is carried out at a temperature of preferably from 20 to 40° C. It is desirable to maintain pH of the medium at around the neutral level. The culturing is carried out generally from a period of from 1 to 5 days.

The metabolite of interest formed and accumulated in the culture medium can be recovered by the following method.

The cells are removed after completion of the culturing, and the metabolite of interest is recovered by a known method such as a concentration crystallization method, an activated carbon treatment method or an ion exchange resin method, see "Bioseparation Process Manual", Isao Endo et al., The Society of Chemical Engineers (edited), Kyoritsu Shuppan (1996).

Examples of the present invention are given below by way of illustration and not by way of limitation.

EXAMPLE 1

Preparation of a Transketolase-deficient Mutant of *Corynebacterium glutamicum*

*Corynebacterium glutamicum* L22 [a lysozyme sensitive mutant derived from a wild strain ATCC 31833; R. Katsumata et al., *Proc. 4th Eur. Congr. Biotechnol.*, 4, 767 (1987)] was inoculated into 3 ml of an NB medium (a medium prepared by dissolving 20 g of bouillon powder and 5 g of yeast extract in 1 L of water and adjusting the medium pH to 7.2) and cultured at 30° C. until $OD_{660}$ became about 0.6.

After the culturing, cells were collected by centrifugation, washed once with 50 mM Tris-maleic acid buffer (pH 6.0)

and then subjected to 20 minutes of mutation treatment at room temperature in 3 ml of the same buffer containing 400 mg/L of NTG.

The treated cells were washed twice by centrifugation using the same buffer and then cultured at 30° C. for 1 hour in 3 ml of the NB medium.

The culture broth thus obtained was diluted by a factor of from $10^{-5}$ to $10^{-6}$ with physiological saline, and 0.1 ml of the diluted culture broth was spread on an NB agar medium (NB medium containing 1.4% agar, pH 7.2) and cultured at 30° C. for 2 days.

Each of the colonies grown on the agar medium was spread and cultured on a minimal agar medium M1 [a medium prepared by dissolving 10 g of glucose, 1 g of $(NH_4)H_2PO_4$, 0.2 g of KCl, 0.2 g of $MgSO_4.7H_2O$, 10 mg of $FeSO_4.7H_2O$, 0.2 mg of $MnSO_4.4-6H_2O$, 0.9 mg of $ZnSO_4.7H_2O$, 0.4 mg of $CuSO_4$ .$5H_2O$, 0.09 mg of $Na_2B_4O_7.10H_2O$, 0.04 mg of $(NH_4)_6Mo_7O_{24}.4H_2O$, 50 mg of biotin, 2.5 mg of p-aminobenzoic acid, 1 mg of thiamin hydrochloride and 16 g of agar in 1 L of water, and adjusting the medium pH to 7.2] and the M1 agar medium supplemented with 50 mg/L of shikimic acid.

Strains which could not grow on the minimal agar medium M1 but were able to grow on the M1 agar medium containing 50 mg/L of shikimic acid were isolated as shikimic acid auxotrophic mutants.

Each shikimic acid auxotrophic mutant thus isolated was spread and cultured on the M1 agar medium containing 50 mg/L of shikimic acid and a medium in which glucose in said medium was replaced by ribose.

Strains which were able to grow on the M1 agar medium containing 50 mg/L of shikimic acid but could not grow on the medium in which glucose in said medium was replaced by ribose were isolated as shikimic acid auxotrophic and ribose non-assimilating mutants.

Each shikimic acid-auxotrophic and ribose non-assimilating mutant thus obtained was cultured in the M1 medium containing 50 mg/L of shikimic acid, and the grown cells were recovered by centrifugation and subjected to a known ultrasonic disintegration method to prepare a crude enzyme solution [M. Ikeda and R. Katsumata, *Appl. Environ. Microbiol.*, 58, 781–785 (1992)].

Using the crude enzyme solution thus prepared, transketolase activity was measured in the following manner.

The crude enzyme solution was added to a reaction solution containing 50 mM of Tris (pH 7.5), 0.2 mM of NADH, 0.01 mM of thiamin pyrophosphate, 1 mM of $MgCl_2$, 0.5 mM of xylose 5-phosphate, 0.5 mM of ribulose 5-phosphate and 20 mg of glycerol-3-phosphate dehydrogenase/triose-phosphate isomerase mixed solution (produced by Boehringer-Mannheim), and the resulting mixture in a total volume of 1.5 ml was subjected to the reaction at 30° C.

The amount of the glyceraldehyde 3-phosphate formed was determined by measuring decreased absorbance of NADH at 340 nm.

By this enzyme assay, a transketolase activity-deficient mutant TKT6 incapable of forming glyceraldehyde 3-phosphate was selected from the mutant strains having shikimic acid auxotrophy and no ribose assimilability.

*Corynebacterium glutamicum* TKT6 was deposited on Jun. 30, 1998, in National Institute of Bioscience and Human Technology, Agency of Industrial Science and Technology, Higashi 1-1-3, Tsukuba, Ibaraki, Japan (Postal Code: 305–0046), under the Budapest Treaty as FERM BP-6399.

EXAMPLE 2
Isolation of Shikimic Acid Non-auxotrophic Revertants

The strain TKT6 was cultured at 30° C. for 24 hours in 3 ml of the NB medium. After the culturing, cells were collected by centrifugation. The cells were washed three times by centrifugation using physiological saline and then suspended in physiological saline to a cell density of about $10^9$/ml.

A 0.1 ml portion of the cell suspension was spread on the M1 agar medium and cultured at 30° C. for 3 days. Strains capable of growing on the M1 agar medium were isolated as shikimic acid non-auxotrophic revertants.

It was found that properties of each shikimic acid non-auxotrophic revertant, including ribose assimilating property and transketolase activity, were restored to those of the wild type.

This result indicates that both characters of shikimic acid auxotrophy and ribose non-assimilating property are induced due to the deficiency of transketolase activity.

One of the shikimic acid non-auxotrophic revertants thus obtained (reverse strains of transketolase deletion mutation) was named REV3.

EXAMPLE 3
Production of Adenine by the *Corynebacterium glutamicum* Transketolase-deficient Mutant Production of adenine by *Corynebacterium glutamicum* L22, TKT6 and REV3 was carried out in the following manner.

Each of the above three strains was inoculated into 3 ml of the NB medium supplemented with 10 g/L of glucose and cultured at 30° C. for 20 hours.

A 0.1 ml portion of each culture broth thus obtained was inoculated into a large test tube containing 5 ml of the M1 medium supplemented with 100 mg/L of shikimic acid and cultured on a shaker at 30° C. for 24 hours.

Each culture broth thus obtained was filtrated, and the amount of adenine formed in the resulting filtrate was determined by measuring the absorbance at 254 nm using an ion exchange column (Shodex Asahipak GS-320 7E, produced by Asahi Chemical Industry) HPLC.

The results are shown in Table 1.

TABLE 1

| Strain | Adenine (mg/L) |
| --- | --- |
| L22 | 0 |
| TKT6 | 117 |
| REV3 | 0 |

Only the transketolase activity-deficient strain TKT6 secreted and accumulated adenine in the culture medium.

Because the transketolase-revertant REV3 obtained from TKT6 again lost the ability to produce adenine, it is obvious that the formation of adenine by TKT6 is ascribed to the deficiency of transketolase.

EXAMPLE 4
Production of L-histidine by the *Corynebacterium glutamicum* Transketolase-deficient Mutant In order to examine the effect of the deficiency of transketolase on the production of histidine by *Corynebacterium glutamicum*, a recombinant plasmid pPH8 containing the histidine-biosynthetic gene was introduced into strains L22, TKT6 and REV3 to improve their histidine productivity, and amounts of histidine produced by the three strains were compared.

The plasmid pPH8 is a plasmid having a spectinomycin resistance marker, in which a DNA fragment of about 10.6 kb having a gene concerned in the biosynthesis of histidine in *Corynebacterium glutamicum* is inserted into the BglII site of a *Corynebacterium glutamicum* plasmid vector pCG11.

The pPH8-carrying *Corynebacterium glutamicum* strain has been deposited in American Type Culture Collection, USA, as *Corynebacterium glutamicum* K32 (ATCC 39281).

The plasmid pPH8 can be isolated from the strain ATCC 39281 by a conventional alkali lysis method [J. Sambrook et al., Molecular Cloning: A Laboratory Manual, 2nd Ed., Cold Spring Harbor Laboratory Press (1989)].

Introduction of pPH8 into strains L22, TKT6 and REV3 can be carried out by a protoplast method generally used in coryneform bacteria [R. Katsumata et al., *J. Bacteriol.*, 159, 306–311 (1984)] or by an electroporation method (voltage 2.5 kV, electric capacity 25 mF, resistance 200 W) [J. Sambrook et al., Molecular Cloning: A Laboratory Manual, 2nd Ed., Cold Spring Harbor Laboratory Press (1989)] using Gene Pulser Apparatus (Bio-Rad Laboratories, Richmond, Calif.), and the protoplast method was used in this test.

Production of histidine by the strains L22, TKT6 and REV3 having pPH8 was carried out in the following manner.

Each of these three strains was inoculated into 3 ml of an S5 seed culture medium (a medium prepared by dissolving 20 g of glucose, 15 g of polypeptone, 15 g of yeast extract, 2.5 g of NaCl and 1 g of urea in 1 L of water and adjusting the solution to pH 7.2) supplemented with 100 mg/L of spectinomycin and the same amount of shikimic acid and cultured on a shaker at 30° C. for 24 hours.

A 0.5 ml portion of each culture thus obtained was inoculated into a large test tube containing 5 ml of a P1 production medium (a medium prepared by dissolving 60 g of glucose, 1 g of $KH_2PO_4$, 1 g of $K_2HPO_4$, 1 g of $MgSO_4.7H_2O$, 20 g of $(NH_4)_2SO_4$, 5 g of corn steep liquor, 10 mg of $MnSO_4$, 30 mg of biotin and 20 g of $CaCO_3$ in 1 L of water and adjusting the solution to pH 7.2) which has been supplemented with 100 mg/L of spectinomycin and 200 mg/L of shikimic acid and cultured on a shaker at 30° C. for 72 hours.

Each culture broth thus obtained was filtered, and the amount of L-histidine formed in the resulting filtrate was determined by the OPA post column derivative formation method [*Anal. Chem.*, 51, 1338 (1979) using HPLC.

The results are shown in Table 2.

TABLE 2

| Strain | L-Histidine (g/L) |
| --- | --- |
| L22/pPH8 | 1.6 |
| TKT6/pPH8 | 3.1 |
| REV3/pPH8 | 1.6 |

The amount of L-histidine produced by TKT6/pPH8 is about two times higher than that of L22/pPH8. On the other hand, the amount of L-histidine produced by REV3/pPH8 is the same level of L22/pPH8, so that it is evident that the improvement of L-histidine productivity in TKT6/pPH8 is ascribed to the deficiency of transketolase.

EXAMPLE 5
Production of Riboflavin by the *Corynebacterium glutamicum* Transketolase-deficient Mutant In order to examine the effect of the deficiency of transketolase on the production of riboflavin by *Corynebacterium glutamicum*, a recombinant plasmid pFM41 containing the riboflavin-biosynthetic gene was introduced into strains L22, TKT6 and REV3 to improve their riboflavin productivity, and amounts of riboflavin produced by the three strains were compared.

The plasmid pFM41 is a plasmid having a spectinomycin resistance marker, in which a DNA fragment of about 4.2 kb having a gene concerned in the biosynthesis of riboflavin in *Corynebacterium ammoniagenes* is inserted into the BglII site of a *Corynebacterium glutamicum* plasmid vector pCG11.

The *Corynebacterium ammoniagenes* having pFM41 has been deposited in National Institute of Bioscience and Human Technology, Agency of Industrial Science and Technology, as *Corynebacterium ammoniagenes* FM41 (FERM BP-4003).

Isolation of plasmid pFM41 from strain FM41 and introduction of pFM41 into strains L22, TKT6 and REV3 were carried out in accordance with the methods described in Example 4.

Production of riboflavin by the strains L22, TKT6 and REV3 having pFM41 was carried out in the following manner.

Each of the three strains was inoculated into 3 ml of the S5 seed culture medium which has been supplemented with 100 mg/L of spectinomycin and the same amount of shikimic acid and cultured on a shaker at 30° C. for 24 hours.

A 0.5 ml portion of each culture thus obtained was inoculated into a large test tube containing 5 ml of the P1 production medium supplemented with 100 mg/L of spectinomycin and 200 mg/L of shikimic acid and cultured on a shaker at 30° C. for 72 hours.

Each culture broth thus obtained was filtered, and the amount of riboflavin formed in the resulting filtrate was determined by measuring fluorescence intensities at an emission wavelength of 530 nm and an excitation wavelength of 450 nm using a reverse phase column (RP-18, produced by Merck) HPLC.

The results are shown in Table 3.

TABLE 3

| Strain | Riboflavin (mg/L) |
| --- | --- |
| L22/pFM41 | 42 |
| TKT6/pFM41 | 108 |
| REV3/pFM41 | 40 |

The amount of riboflavin produced by TKT6/pFM41 is about two times higher than that of L22/pFM41. On the other hand, the amount of riboflavin produced by REV3/pFM41 is the same level of L22/pFM41, so that it is evident that the improvement of riboflavin productivity in TKT6/pFM41 is ascribed to the deficiency of transketolase.

EXAMPLE 6
Production of Riboflavin by the *Escherichia coli* Transketolase Activity-reduced Mutant In order to examine the effect of the deficiency of transketolase on the production of riboflavin by *Escherichia coli*, a recombinant plasmid pFM201 containing the riboflavin-biosynthetic gene was introduced into an *Escherichia coli* strain EJ500 and its transketolase-defective strain AI80 to provide the strains with riboflavin productivity, and amounts of riboflavin produced by both recombinant strains were compared.

The strain AI80 is a transketolase-defective strain obtained from the strain EJ500 (W3100 cfs) by Tn10 insertion, in which its transketolase activity was reduced to about 30% of the parent strain due to destruction of one of the two transketolase genes, tktA gene, by the insertion of Tn10 [A. Iida et al., *J. Bacteriol.*, 175, 5375–5383 (1993)].

The plasmid pFM201 is a plasmid having an ampicillin resistance marker, in which a DNA fragment having a gene concerned in the biosynthesis of riboflavin in *Corynebacterium ammoniagenes* is inserted into the downstream site of lac promoter of pUC19, and was prepared in accordance with the method described in JP-A-6-225776.

Introduction of pFM201 into strains EJ500 and AI80 can be carried out by a usual electroporation method or by a calcium method [J. Sambrook et al., Molecular Cloning: A Laboratory Manual, 2nd Ed., Cold Spring Harbor Laboratory Press (1989)], and the calcium method was used in this test.

Production of riboflavin by the strains EJ500 and AI80 having pFM201 was carried out in the following manner.

Each of the two strains was inoculated into 3 ml of an LB medium (a medium prepared by dissolving 10 g of Bactotryptone, 5 g of yeast extract and 5 g of NaCl in 1 L of water and adjusting the solution to pH 7.2) which has been supplemented with 100 mg/L of ampicillin and cultured on a shaker at 30° C. for 16 hours.

A 0.1 ml portion of each culture broth thus obtained was inoculated into a large test tube containing 5 ml of a P6 production medium (a medium prepared by dissolving 5 g of glucose, 3 g of $KH_2PO_4$, 0.25 g of $MgSO_4 \cdot 7H_2O$, 5 g of NaCl, 1 g of $NH_4Cl$, 6 g of $NaHPO_4$ and 4 mg of thiamin hydrochloride in 1 L of water and adjusting the solution to pH 7.2) which has been supplemented with 100 mg/L of ampicillin and the same amount of shikimic acid and cultured on a shaker at 37° C. for 24 hours.

The amount of riboflavin formed in the resulting filtrates was determined using HPLC in accordance with the method described in Example 5.

The results are shown in Table 4.

TABLE 4

| Strain | Riboflavin (mg/L) |
|---|---|
| EJ500/pFM201 | 14 |
| AI80/pFM201 | 25 |

The amount of riboflavin produced by AI80/pFM201 is about 1.8 times higher than that of EJ500/pFM201, showing that productivity of riboflavin is improved by reducing the transketolase activity.

According to the present invention, an industrially more advantageous method for the production of metabolites biologically synthesized via PRPP is provided, making use of metabolically modified strains in which the transketolase activity is deficient or reduced in comparison with the parent strain.

While the invention has been described in detail and with reference to specific embodiments thereof, it will be apparent to one skilled in the art that various changes and modifications can be made therein without departing from the spirit and scope thereof.

This application is based on Japanese patent application No. Hei. 10-187992, filed on Jul. 3, 1998, and incorporated herein by reference.

What is claimed is:

1. A method for increasing productivity of metabolites biologically synthesized via phosphoribosyl pyrophosphate on metabolic pathway, which comprises the steps of:

selecting a parent strain of microorganism belonging to the genus Corynebacterium, Brevibacterium or Escherichia having transkelolase activity;

reducing or inactivating said transketolase activity in comparison to that of said parent strain; and detecting increase in productivity of phosphoribosyl pyrophosphate in said microorganism in comparison to that of said parent strain.

2. A method for producing metabolites, which comprises the steps of:

culturing in a medium a microorganism belonging to the genus Corynebacterium, Brevibacterium or Escherichia said microorganism having transketolase activity which is deficient or reduced in comparison with a parent strain thereof;

forming and accumulating in the culture at least one metabolite including phosphoribosyl pyrophosphate biologically synthesized on the metabolic pathway via phosphoribosyl pyrophosphate; and recovering said metabolites therefrom.

3. The method according to claim 1 or 2, wherein the metabolite is selected from the group consisting of purine nucleotides, pyrimidine nucleotides, purine nucleosides, pyrimidine nucleosides, purine bases, pyrimidine bases, flavin nucleotides, L-histidine and riboflavin.

4. The method according to claim 1 or 2, wherein said microorganism is selected from the group consisting of *Corynebacterium glutamicum* TKT6, *Corynebacterium glutamicum* TKT6/pPH8, *Corynebacterium glutamicum* TKT6/pFM41 and *Escherichia coli* AI80/pFM201.

5. An isolated microorganism belonging to the genus Corynebacterium, in which transketolase activity is deficient or reduced in comparison with a parent strain thereof, wherein said microorganism is selected from the group consisting of *Corynebacterium glutamicum* TKT6, *Corynebacterium glutamicum* TKT6/pPH8 and *Corynebacterium glutamicum* TKT6/pFM4 1.

6. The method according to claim 1, wherein said microorganism is Brevibacterium.

7. The method according to claim 1, wherein said microorganism is Escherichia.

8. The method according to claim 3, wherein said microorganism is selected from the group consisting of *Corynebacterium glutamicum* TKT6, *Corynebacterium glutamicum* TKT6/pPH8, *Corynebacterium glutamicum* TKT6/pFM41 and *Escherichia coli* AI80/pFM201.

* * * * *

UNITED STATES PATENT AND TRADEMARK OFFICE
CERTIFICATE OF CORRECTION

PATENT NO.    : 6,258,554 B1
DATED         : July 10, 2001
INVENTOR(S)   : Masato Ikeda et al.

It is certified that error appears in the above-identified patent and that said Letters Patent is hereby corrected as shown below:

<u>Title page,</u>
Item [22], Filing Date, "July 22, 1999" should read -- July 2, 1999 --.

<u>Column 2,</u>
Line 66, "coil" should read -- coli --.

<u>Column 5,</u>
Line 47, "such-as" should read -- such as --.

<u>Column 7,</u>
Line 48, "MgCl$_2$." should read -- MgCl$_2$, --.

<u>Column 12,</u>
Line 22, "chia" should read -- chia, --; and
Line 46, "TKT6/pFM4 1." should read -- TKT6/pFM41. --.

Signed and Sealed this

Second Day of April, 2002

Attest:

JAMES E. ROGAN
*Attesting Officer*    *Director of the United States Patent and Trademark Office*